(12) United States Patent
Werle et al.

(10) Patent No.: US 8,198,431 B2
(45) Date of Patent: Jun. 12, 2012

(54) PROCESS FOR PREPARING TRIALLYL ISOCYANURATE (TAIC)

(75) Inventors: Peter Werle, Gelnhausen (DE); Hans-Peter Krimmer, Kichweidach (DE); Manfred Schmidt, Gelnhausen (DE); Klaus Stadtmueller, Alzenau (DE); Martin Trageser, Gelnhausen-Hoechst (DE)

(73) Assignee: Evonik Degussa GmbH, Essen (DE)

( * ) Notice: Subject to any disclaimer, the term of this patent is extended or adjusted under 35 U.S.C. 154(b) by 677 days.

(21) Appl. No.: 12/307,592

(22) PCT Filed: Jun. 14, 2007

(86) PCT No.: PCT/EP2007/055879
§ 371 (c)(1),
(2), (4) Date: Jan. 6, 2009

(87) PCT Pub. No.: WO2008/006661
PCT Pub. Date: Jan. 17, 2008

(65) Prior Publication Data
US 2009/0312545 A1  Dec. 17, 2009

(30) Foreign Application Priority Data
Jul. 12, 2006 (DE) .......................... 10 2006 032 167

(51) Int. Cl.
*C07D 487/22* (2006.01)
*C07B 47/00* (2006.01)
(52) U.S. Cl. ..................................... 540/145
(58) Field of Classification Search .................. 544/180; 540/145
See application file for complete search history.

(56) References Cited

U.S. PATENT DOCUMENTS

| 3,322,761 A | 5/1967 | Little |
| 4,451,651 A | 5/1984 | Brand |

FOREIGN PATENT DOCUMENTS

| DE | 28 39 084 | 3/1979 |
| EP | 0 078 567 | 5/1983 |
| SU | 1121259 | 12/1982 |
| SU | 1121260 | 12/1982 |

OTHER PUBLICATIONS

Likhterov et al., Chem of Het Comp., vol. 24, No. 3, 1988, pp. 308-311.*
Database WPI/Derwent Pub. (Database accession # 1985-126915).*
Database WPI/Derwent Pub. (Database accession # 1985-126916).*
Likhterov, V. et al., Inter-And Intramolecular Rearrangements of Cyanuric Acid Triallyl Esters, Translated From Khimiya Geterotsiklicheskikh Soedinenii, vol. 24, No. 3, pp. 308-311, XP009091781, (1988).
Balitskaya, L.G. et al., "Isomerization of Cyanurates in the Presence of Copper", Ukrainskii Khimicheskii Zhurnal, vol. 40, No. 8, pp. 881-882, XP009091782, (1974).

* cited by examiner

*Primary Examiner* — Paul V. Ward
(74) *Attorney, Agent, or Firm* — Oblon, Spivak, McClelland, Maier & Neustadt, L.L.P.

(57) ABSTRACT

The invention is directed to an improved, reliably performable process for preparing triallyl isocyanurate (TAIC) by $Cu^{2+}$-catalysed rearrangement of triallyl cyanurate (TAC) at at least 90° C. According to the invention, TAC and, if required, also a $Cu^{2+}$ catalyst and solvent are fed continuously to a start reaction mixture after onset of the initially inhibited isomerization reaction, the isomerization is performed at from 90 to 160° C. and an amount of reaction mixture equivalent to the amount of reactant is drawn off continuously and sent to the workup. Preference is given to effecting the isomerization in TAIC as the reaction medium.

16 Claims, No Drawings

PROCESS FOR PREPARING TRIALLYL ISOCYANURATE (TAIC)

The invention is directed to an improved, reliably performable process for preparing triallyl isocyanurate (TAIC) by $Cu^{2+}$-catalysed rearrangement of triallyl cyanurate (TAC) at at least 90° C.

Triallyl isocyanurate [triallyl-s-triazine-2,4,6(1H,3H,5H)-trione; referred to as TAIC in abbreviated form] is a trifunctional polymerizable monomer which finds use as a crosslinking component for high-value thermoplastics and synthetic rubber, and also as a raw material for the production of flame retardants. Moreover, TAIC also finds use as a copolymerization component in the polymerization of vinylic, allylic and acrylic monomers.

TAIC can be prepared essentially by three methods:

In the process according to U.S. Pat. No. 3,322,761, triallyl isocyanurate (TAIC) is obtained by reacting cyanuric acid with allyl chloride and sodium hydroxide in the presence of copper chloride as a catalyst. A disadvantage in this process is the high excess of allyl chloride (6 mol/mol of cyanuric acid), the formation of allyl alcohol and diallyl isocyanurate as hydrolysis products, and the complicated removal and purification of the TAIC obtained.

An industrially more useful route to the preparation of TAIC is the trimerization of allyl isocyanate formed in situ. In this case, as described by way of example in JP 52-109627 or DE-A 28 39 084, an alkali metal cyanate is reacted with allyl chloride in a dipolar aprotic solvent, preferably dimethylformamide, at temperatures around 130° C. Although the process affords good yields, a disadvantage is the occurrence of large amounts of organically contaminated sodium chloride, the use of toxic solvents and the quite expensive purification steps which are needed in order to provide a TAIC quality which satisfies market requirements.

A third method for the preparation of TAIC is the Claisen rearrangement of triallyl cyanurate (TAC), which is itself obtained on the industrial scale by reaction of cyanuric chloride with allyl alcohol, in the presence of catalysts (cat.).

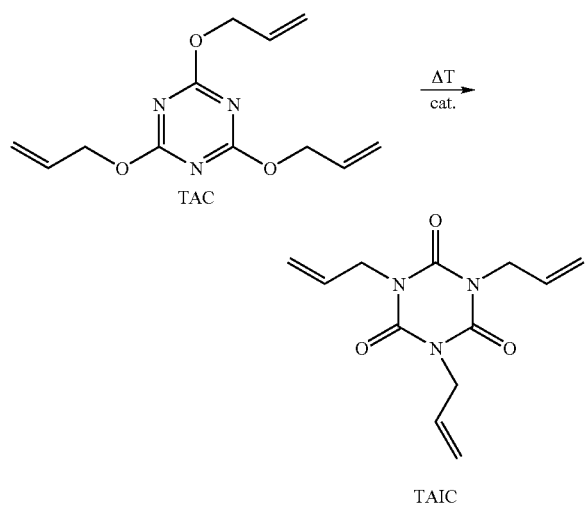

In the process according to EP 0 078 567 A1, the rearrangement of TAC to TAIC is performed in the presence of quaternary ammonium compounds. Disadvantages in this process are the long reaction times and the risk of spontaneous polymerization of the entire mixture. In the reworking of the process by the inventors of the present application, polymerization with temperatures of >200° C. and vigorous evolution of smoke occurred after a few minutes.

The isomerization of cyanurates to isocyanurates in the presence of metallic copper is described by Balitskaya et al. in Ukr. Khim. Zh. 40(8), 881, (1974). In the presence of 20% copper, the rearrangement of TAC to TAIC at 70° C. is said to have ended within 5 h. Attempts of the inventors of the present application and also of EP 0 078 567 A1, in contrast, did not lead to any such result.

SU patent 1121259 teaches a process for preparing TAIC by isomerizing TAC in toluene in the presence of copper and a reducing agent from the group of tin(II) chloride and iron(II) chloride at temperatures of 95 to 130° C. The molar ratios of the components here are: TAC (1); toluene (1.3-4.1); copper (0.39-0.8); reducing agent (0.0013-0.0026). Depending on the temperature and the catalyst concentration, the reaction times are 1 to 20 h. Disadvantages here are the very high catalyst use and the long reaction times.

SU patent 1121260 claims the isomerization of TAC to TAIC in toluene as a solvent using a Cu salt, such as $CuCl_2.2H_2O.CuAc_2.2H_2O$, CuCl, $CuSO_4.5H_2O$, $CuF_2.2H_2O$, $Cu(NO_3)_2.3H_2O$ and CuBr, as a catalyst. The molar TAC:toluene:catalyst ratios are specified as 1: (1.3-4): (0.0015-0.0073). The processes of SU 1121259 and SU 1121260 are performed batchwise, catalyst being initially charged in a glass reactor and being admixed with a portion of a solution of TAC in toluene. After heating to about 100° C., the remaining amount of the TAC/toluene mixture is added within 3 h and the reaction is continued for 2 h; thereafter, the reaction mixture is worked up by distillation.

In the reworking of the process of SU 1121260, it has been found that the procedure described cannot be operated reliably and safely for a preparation of the triallyl isocyanurate on the industrial scale. Even though the SU document teaches the use of a minimum amount of toluene in order to prevent an explosion-like process, uncontrollable process states occurred in the reworking of the process. This document does not give any information as to how the process can be operated on the industrial scale and continuously without any safety risk.

A further disadvantage of the process described in SU 1121260 is the formation of polymerization products: since the TAIC remains in the reactor over a long period, it is possible, as the inventors of the present application have found, for up to 20% by weight of oligomers to form, which are not detectable in the gas chromatogram but give rise to a precipitate with methanol after the solvent has been distilled off. It has also been found that the use of the hydrate-containing Cu salts taught in the SU document leads either to an unsatisfactory conversion or to the formation of a by-product. As experiments by the Applicant have found, water eliminates allyl alcohol from TAC under the catalytic action of the copper salts, so that diallyl isocyanurate is formed as a by-product.

It is accordingly an object of the invention to indicate the provision of an improved and reliably performable process for preparing TAIC by Cu salt-catalysed rearrangement of TAC. The process should be simple to perform. In a further object, embodiments by which the use of solvent can be minimized should also be indicated. In a further object, TAIC should be obtainable in high yield and high purity. In a further object, the process should largely avoid the formation of oligomeric and polymeric by-products.

The aforementioned objects and further objects as are evident from the description are achieved by the process according to the invention according to the main claim and in particular embodiments according to the subclaims. The process according to the invention is a continuous process which overcomes the problems of the batch process.

A process has been found for preparing triallyl isocyanurate (TAIC), comprising rearrangement of triallyl cyanurate (TAC) in the presence of a Cu salt at a temperature of at least 90° C., which is characterized in that TAC and a $Cu^{2+}$ salt are introduced continuously in an amount of 0.01 to 1% by weight of $Cu^{2+}$, based on TAC, separately from one another or in the form of a mixture comprising these components, into a TAIC-containing reaction mixture which has been formed at at least 90° C. by rearrangement of TAC in the presence of a $Cu^{2+}$ salt and has not been cooled below 90° C. thereafter, the rearrangement is performed under these conditions while maintaining a temperature in the range of 90 to 160° C. and an amount of reaction mixture corresponding to the addition is discharged continuously and TAIC is isolated therefrom.

The isomerization of TAC to TAIC under Cu salt catalysis is, as has been found, very probably an auto-catalytic process with an incubation time which depends upon the type of catalyst used, upon the catalyst concentration, upon the temperature and upon the solvent used.

The isomerization proceeds with release of 700 kJoule/kg of TAC. Measurements in a Contraves calorimeter additionally showed that more than 90% of the total exothermicity is released within approx. 5 min. This behaviour led to the indicated problems of the process known to date. These problems are solved by the process according to the invention.

In the process according to the invention, the start phase and hence the composition of the start mixture of the reaction are highly significant with regard to safe performance of the overall reaction. It is important that the start mixture originated from the $Cu^{2+}$-catalysed isomerization of TAC to TAIC and had not been cooled to a temperature below 90° C. before use. Cooling of the start mixture comprising TAIC and $Cu^{2+}$ to values below 90° C. deactivates the catalyst or catalyst complex; simple heating of the mixture does not result in reactivation; instead, another incubation time has to be passed through after adding TAC. Use of an inventive reaction mixture into which TAC is introduced continuously prevents spontaneous reactions which may occur before the incubation time has ended and may be uncontrollable.

In a particular embodiment, the isomerization is performed in the presence of a polymerization inhibitor; examples are hydroquinone, hydroquinone monomethyl ether, tert-butylated phenols and alkyl-phenols. Such inhibitors are often already present in the TAC.

The dependence of the incubation time upon the catalyst concentration in toluene as the solvent follows from Table 1.

TABLE 1

Dependence of the incubation time upon the catalyst concentration

| $Cu^{2+}$ conc. [%] | Incubation time [min] |
|---|---|
| 0.5 | 13-14 |
| 0.4 | 17 |
| 0.3 | 20 |
| 0.2 | 28 |
| 0.1 | >35 |

The measurements were effected in 100 ml flasks which were present in a silicone bath at 120±2° C. The commencement of the isomerization is recognizable by a sudden temperature rise which leads to vigorous boiling of the entire flask contents. Gas chromatography analyses show consistently that virtually no reaction has taken place beforehand. The TAC:toluene volume ratio was 1:2; the catalyst used was $CuCl_2.2H_2O$; the amount in % is based on TAC.

Apart from aromatic hydrocarbons, there are, as has been found, further solvent groups in which the isomerization can be performed. Apart from toluene, suitable solvents are aprotic solvents which are stable with respect to a combination of $Cu^{2+}$ and TAC, such as aliphatic, cycloaliphatic or aromatic hydrocarbons, diesters of carbonic acid, aromatic and aliphatic carboxylic acid esters and ethers. In a preferred embodiment, TAIC itself serves as a solvent and means of evaporative cooling. Table 2 shows some solvents and the incubation times determined with them.

TABLE 2

Isomerization in various solvents.

| | Incubation time [min] | |
|---|---|---|
| Solvent | 0.4% | 0.25% |
| Butyl acetate | 9-10 | 14-16 |
| Isobutyl acetate | | 14 |
| Diethyl carbonate | 10-11 | 15-17 |
| Ethylene glycol diethyl ether | 18 | |
| Toluene | 17 | 22-23 |
| Petroleum ether | | 17-19 |
| Octane | | 18 |
| Xylene | | 20-27 |
| Diethylene glycol dimethyl ether | | 17 |

TAC:solvent volume ratio = 1:2, catalyst $Cu^{2+}$; concentration 0.4% or 0.25% $Cu^{2+}$ The selection of the solvents is, when operation is not to be effected under pressure, determined by the boiling temperature, which should preferably be in the range of 110 to 160° C. A reaction temperature of 110 to 140° C. has been found to be favourable. Higher-boiling solvents such as TAIC can be transferred into the favourable working range by applying a vacuum. Alcohols, ketones, acid anhydrides and many dipolar aprotic solvents are less suitable or completely unsuitable since they form by-products.

All of the problems which afflict the isomerization of TAC are circumvented by the continuous process according to the invention, since operation is effected here with small operating volumes and very short residence times. This minimizes the risk potential of a spontaneous polymerization and prevents polymerization as a result of long thermal stress.

The basis of the process is the discovery that a reaction, once it has set in in a $Cu^{2+}$-containing start reaction mixture, can be maintained by supplying TAC or a mixture of TAC and solvent in which catalyst may additionally be dissolved or be dispersed ultrafine, when an amount equivalent to the amount supplied can simultaneously be withdrawn from the reaction vessel, specifically in the form of distilled-off TAIC or in the form of a solution of TAIC and $Cu^{2+}$ catalyst in the particular solvent.

Copper(II) chloride exhibits the surprising property of dissolving readily in mixtures of toluene and TAC with a blue colour but only poorly in the pure starting components. This system is therefore particularly preferred, also owing to the ready availability of $CuCl_2$. Sparingly soluble $Cu^{2+}$ catalysts can be used for the continuous process only when they have been ground to microfine particles by suitable dispersion units before or during the reaction.

In a preferred embodiment, the $Cu^{2+}$ catalyst used is an anhydrous salt, especially a salt from the group of $CuCl_2$, $CuBr_2$, $CuI_2$, $Cu(RCOO)_2$ where R=alkyl or aryl. Typically, the rearrangement is performed in the presence of 0.01 to 1% by weight of $Cu^{2+}$, in particular 0.02 to 0.2% by weight of $Cu^{2+}$, based on the TAIC present in the start reaction mixture converted—TAC has been converted virtually quantitatively a few minutes after its addition. When catalyst-containing reaction mixture is drawn off to the degree in which TAC and solvent are supplied, the catalyst concentration also has to be maintained by supplying catalyst.

In a preferred embodiment, the reaction is performed in the absence of an extraneous solvent, i.e. TAIC is the reaction medium. In this case, TAC is introduced continuously into a TAIC-containing start reaction mixture which has been formed at at least 90° C. by rearrangement of TAC in the presence of a $Cu^{2+}$ salt and has not been cooled below 90° C. thereafter, the rearrangement is performed at 90 to 160° C., in particular 110 to 140° C., and TAIC which forms is distilled continuously out of the reaction mixture under reduced pressure, the addition rate of TAC (g of TAC/min) corresponding essentially to the distillation rate of TAIC (g of TAIC/min). Advantages of this embodiment are dispensing with an extraneous solvent, the use of catalyst only once and the simple workup.

In a preferred embodiment, the process according to the invention can be implemented by the following process steps:

Start reaction: A mixture of TAC, solvent and catalyst is introduced into a reaction vessel. The TAC:solvent:$Cu^{2+}$ ratio, in order to reliably capture the exothermicity and allow a relatively rapid start, is selected at about 250 ml of TAC:750 ml of solvent:3 g of $CuCl_2$ per litre of solution. The reactor is heated to internal temperature 110 to 115° C. and stirred. After approx. 15 to 17 min, the rearrangement to TAIC sets in, which is recognized by vigorous boiling of the reactor contents.

Continuous method: Once the reaction has set in, a mixture of TAC, solvent and catalyst is pumped continuously into the reactor, specifically in such an amount that the mean residence time of the TAC is not less than approx. 10 min and not more than 60 min. The amount of solvent in the solution supplied is variable within wide limits, but the content of solvent is preferably reduced in order to reduce distillation work.

It is in principle also possible to work without solvent; in this case, the TAIC which forms serves as the reaction medium, and the heat of isomerization is removed here by evaporative cooling under reduced pressure. The ratio of the reactants can vary in the TAC:solvent volume ratio of about 1:4 to 1:0. The catalyst concentration can, once the reaction has set in (start reaction), be lowered very greatly. Concentrations of 0.15 g of $Cu^{2+}$ per litre of reactant solution are still effective.

Isolation of the TAIC: The same amount of TAIC/solvent/catalyst is synchronously pumped out of the reactor as that in which reactants are added. When $CuCl_2$ and toluene or diethyl carbonate are used, the incoming TAC solution has a blue colour, the withdrawn TAIC solution a green colour. The reaction is monitored by gas chromatography. Once the solvent has been distilled off, the TAIC is purified by vacuum distillation. The bottom effluent contains the $Cu^{2+}$. In a particular embodiment of the process, disposal of the $Cu^{2+}$ can be largely dispensed with: in this case, the bottoms of the vacuum distillation, whose proportion is set somewhat higher, are pumped directly and while still hot to the reaction vessel, and ensure the maintenance of the catalyst concentration here. However, the activity is preserved only when the temperature of the bottom is kept at at least 90° C.; after cooling of the bottom to room temperature and reheating, the reaction can no longer be maintained.

The process according to the invention can be performed reliably and without risk of a spontaneous reaction. A rapid reaction and continuous method largely avoid the formation of by-products and oligomers.

The examples which follow are intended to illustrate the process in detail:

EXAMPLE 1

A solution of 25 ml of TAC, 0.3 g of $CuCl_2$ (anhydrous) in 75 ml of toluene was introduced into a jacketed stirred vessel of capacity 500 ml, which was heated by a thermostatted silicone bath adjusted to 130° C. The internal flask temperature was adjusted to 113 to 115° C. After 16 min, vigorous reflux set in; the initially blue solution had been converted to a dark olive green solution. After the reaction had abated, 10 ml/min of a mixture of 3000 ml of TAC, 3.0 g of $CuCl_2$ and 3000 ml of toluene were pumped in continuously by means of a metering pump. At the same time, 10 ml/min of the reaction solution were withdrawn by means of a 2nd metering pump. The reaction temperature rose to approx. 123 to 125° C.

When the system is operated with higher TAC concentration (higher space-time yield), the reaction temperature is limited to max. 140° C. by applying an appropriate vacuum.

The conversion rate was >99.9%. The by-product formed by residual water in TAC and toluene was a little diallyl isocyanurate. The process was operated without any problem over a period of 10 h.

EXAMPLE 2

Process according to Example 1, except that diethyl carbonate was used as the solvent. The reaction mixture for the start reaction was prepared by mixing TAC with diethyl carbonate in a volume ratio of 1 to 3 and adding 2.5 g of $CuCl_2$ per litre of reactant solution, and then ultrafine grinding in a wet mill. After initially charging 200 ml of this solution, heating to 130° C. and waiting for the start reaction, 15 ml/min of a homogeneous dispersion of TAC and diethyl carbonate in a volume ratio of 1 to 1 and 0.4 g of $CuCl_2$ per litre of solution were pumped in and, in parallel, 15 ml/min of green TAIC solution were withdrawn. The conversion of the TAC was >99.8%. This procedure was maintained over a period of 8 h without disruption or decline in the yield and purity.

EXAMPLE 3

Process according to Example 1, except that, after the onset of the start reaction, a homogeneous, ultrafine-dispersed mixture of 1000 ml of TAC and 0.25 g of anhydrous $CuCl_2$ was metered in. The amount metered in was 10 ml/min; at the same time, 10 ml/min of reaction solution were pumped out. Since the reaction vessel had become low in toluene in the course of time as a result of distilling-off toluene, the operating temperature in the reactor rose continually. In order to prevent polymerization, a vacuum was applied at internal flask temperature 140° C. in order to maintain a constant working temperature through evaporative cooling of the TAIC formed. The vacuum necessary for this purpose was 2.0 to 3.0 hpa. This process afforded TAIC with a purity of 98.5%; the isomerization rate of the TAIC was >99.8%.

The invention claimed is:
1. A process for preparing triallyl isocyanurate (TAIC), comprising rearrangement of triallyl cyanurate (TAC) in the presence of a Cu salt at a temperature of at least 90° C., wherein

TAC and a $Cu^{2+}$ salt are introduced continuously in an amount of 0.01 to 1% by weight of $Cu^{2+}$, based on TAC, separately from one another or in the form of a mixture comprising these components, into a TAIC-containing reaction mixture which has been formed at at least 90° C. by rearrangement of TAC in the presence of a $Cu^{2+}$ salt and has not been cooled below 90° C. thereafter, the rearrangement is performed under these conditions while maintaining a temperature in the range of 90 to 160° C. and an amount of reaction mixture corresponding to the addition is discharged continuously and TAIC is isolated therefrom.

2. The process according to claim 1, wherein the rearrangement of TAC to TAIC is performed in the presence of an aprotic solvent which is stable at 90 to 160° C. with respect to a combination of $Cu^{2+}$ and TAC.

3. The process according to claim 1,
wherein
TAC and, if required, additionally $Cu^{2+}$ salt are introduced into the reaction mixture in the form of an aprotic solvent which is stable at 90 to 160° C. with respect to a combination of $Cu^{2+}$ and TAC.

4. The process according to claim 2,
wherein
TAC and a $Cu^{2+}$ salt are introduced separately or in a mixture, where the individual components or the mixture may additionally comprise an aprotic solvent which is stable at the reaction temperature with respect to a combination of $Cu^{2+}$ and TAC, into a TAIC-containing reaction mixture which has been formed at 90 to 160° C. by rearrangement of TAC in the presence of a $Cu^{2+}$ salt and of an aprotic solvent which is stable at the reaction temperature mentioned with respect to a combination of $Cu^{2+}$ and TAC.

5. The process according to claim 2,
wherein
the aprotic solvent used is an aliphatic, cycloaliphatic or aromatic hydrocarbon, a diester of carbonic acid, an ester of an aliphatic or aromatic carboxylic acid or an ether.

6. The process according to claim 1,
wherein
the rearrangement is performed at a temperature in the range from 110 to 140° C.

7. The process according to claim 1,
wherein
the $Cu^{2+}$ salt used is an anhydrous salt, especially a salt from the group of $CuCl_2$, $CuBr_2$, $CuI_2$, $Cu(RCOO)_2$ where R=alkyl or aryl.

8. The process according to claim 7,
wherein
the catalyst fed continuously to the reaction mixture is $CuCl_2$ in an amount of 0.02 to 0.2% by weight of $Cu^{2+}$, based on TAC.

9. The process according to claim 1,
wherein
the $Cu^{2+}$ salt fed in continuously is a bottom product which has been obtained by distilling TAIC out of the reaction mixture drawn off continuously, the temperature of the bottom product not having been cooled to a temperature of below 90° C. before its reuse.

10. A process for preparing TAC, comprising rearrangement of triallyl cyanurate (TAC) in the presence of a Cu salt at a temperature of at least 90° C.,
wherein
TAC is introduced continuously into a TAIC-containing start reaction mixture which has been formed at at least 90° C. by rearrangement of TAC in the presence of a $Cu^{2+}$ salt and has not been cooled below 90° C. thereafter, the rearrangement is performed under these conditions while maintaining a temperature in the range of 90 to 160° C., and TAIC which forms is distilled continuously out of the reaction mixture under reduced pressure, the addition rate of TAC (g of TAC/min) corresponding essentially to the distillation rate of TAIC (g of TAIC/min).

11. The process according to claim 10,
wherein
the rearrangement is performed in the presence of 0.01 to 1% by weight of $Cu^{2+}$, based on the TAC used to prepare the start reaction mixture.

12. The process according to claim 10,
wherein
the rearrangement is performed at 110 to 140° C.

13. The process according to claim 10,
wherein
TAC is added at such a rate that the TAIC distilled off is virtually free of unconverted TAC.

14. The process according to claim 2,
wherein
TAC and, if required, additionally $Cu^{2+}$ salt are introduced into the reaction mixture in the form of an aprotic solvent which is stable at 90 to 160° C. with respect to a combination of $Cu^{2+}$ and TAC.

15. The process according to claim 3,
wherein
TAC and a $Cu^{2+}$ salt are introduced separately or in a mixture, where the individual components or the mixture may additionally comprise an aprotic solvent which is stable at the reaction temperature with respect to a combination of $Cu^{2+}$ and TAC, into a TAIC-containing reaction mixture which has been formed at 90 to 160° C. by rearrangement of TAC in the presence of a $Cu^{2+}$ salt and of an aprotic solvent which is stable at the reaction temperature mentioned with respect to a combination of $Cu^{2+}$ and TAC.

16. The process according to claim 11,
wherein
the rearrangement is performed at 110 to 140° C.

\* \* \* \* \*

UNITED STATES PATENT AND TRADEMARK OFFICE
CERTIFICATE OF CORRECTION

| | |
|---|---|
| PATENT NO. | : 8,198,431 B2 |
| APPLICATION NO. | : 12/307592 |
| DATED | : June 12, 2012 |
| INVENTOR(S) | : Peter Werle et al. |

It is certified that error appears in the above-identified patent and that said Letters Patent is hereby corrected as shown below:

On the title page, Item (75), the second inventor's city of residence is incorrect. Item 75 should read:

--(75) Inventor: Hans-Peter Krimmer, Kirchweidach (DE);

Signed and Sealed this
Eleventh Day of September, 2012

David J. Kappos
*Director of the United States Patent and Trademark Office*